United States Patent

Reuven

[11] Patent Number: 5,960,506
[45] Date of Patent: Oct. 5, 1999

[54] PUMICE SCRUBBING PAD

[76] Inventor: Michelle G. Reuven, 4219 E. 4th St. Apt. #5, Long Beach, Calif. 90814

[21] Appl. No.: 09/036,415
[22] Filed: Mar. 5, 1998
[51] Int. Cl.⁶ .............................. A47K 7/03; A47L 13/17
[52] U.S. Cl. ..................................... 15/104.93; 15/229.12
[58] Field of Search ........................... 15/104.93, 104.94, 15/208, 209.1, 229.11, 229.12, 229.13; 401/201; 601/136–138, 143, 147

[56] References Cited

U.S. PATENT DOCUMENTS

| 2,395,068 | 2/1946 | Rimer | 15/104.93 |
| 2,432,091 | 12/1947 | Englund | 15/104.93 X |
| 2,447,241 | 8/1948 | Englund | 15/229.12 |

FOREIGN PATENT DOCUMENTS 1093900  12/1967  United Kingdom ................ 15/104.93

*Primary Examiner*—Mark Spisich

[57] ABSTRACT

A new pumice scrubbing pad for removing rough and dead skin from feet. The inventive device includes a plurality of filaments which are aggregated to form a pad member having spaces therein. Provided on the outer surface of the filaments is a scrubbing coating. The scrubbing coating includes a plurality scrubbing particles, a soap, a skin moisturizing agent, a fragrance, and a binder which couples the scrubbing coating to the outer surfaces of the filaments.

9 Claims, 2 Drawing Sheets

PUMICE SCRUBBING PAD

BACKGROUND OF THE INVENTION

1. Field of the Invention

The present invention relates to scrubbing pads and more particularly pertains to a new pumice scrubbing pad for removing rough and dead skin from feet.

2. Description of the Prior Art

The use of scrubbing pads is known in the prior art. More specifically, scrubbing pads heretofore devised and utilized are known to consist basically of familiar, expected and obvious structural configurations, notwithstanding the myriad of designs encompassed by the crowded prior art which have been developed for the fulfillment of countless objectives and requirements.

Known prior art scrubbing pads include U.S. Pat. No. 4,933,306; U.S. Pat. No. 5,090,832; U.S. Pat. No. 4,712,552; U.S. Pat. No. 4,959,881; U.S. Pat. No. 4,536,911; and U.S. Pat. No. Des. 345,627.

While these devices fulfill their respective, particular objectives and requirements, the aforementioned patents do not disclose a new pumice scrubbing pad. The inventive device includes a plurality of filaments which are aggregated to form a pad member having spaces therein. Provided on the outer surface of the filaments is a scrubbing coating. The scrubbing coating includes a plurality scrubbing particles, a soap, a skin moisturizing agent, a fragrance, and a binder which couples the scrubbing coating to the outer surfaces of the filaments.

In these respects, the pumice scrubbing pad according to the present invention substantially departs from the conventional concepts and designs of the prior art, and in so doing provides an apparatus primarily developed for the purpose of removing rough and dead skin from feet.

SUMMARY OF THE INVENTION

In view of the foregoing disadvantages inherent in the known types of scrubbing pads now present in the prior art, the present invention provides a new pumice scrubbing pad construction wherein the same can be utilized for removing rough and dead skin from feet.

The general purpose of the present invention, which will be described subsequently in greater detail, is to provide a new pumice scrubbing pad apparatus and method which has many of the advantages of the scrubbing pads mentioned heretofore and many novel features that result in a new pumice scrubbing pad which is not anticipated, rendered obvious, suggested, or even implied by any of the prior art scrubbing pads, either alone or in any combination thereof.

To attain this, the present invention generally comprises a plurality of filaments which are aggregated to form a pad member having spaces therein. Provided on the outer surface of the filaments is a scrubbing coating. The scrubbing coating includes a plurality scrubbing particles, a soap, a skin moisturizing agent, a fragrance, and a binder which couples the scrubbing coating to the outer surfaces of the filaments.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new pumice scrubbing pad apparatus and method which has many of the advantages of the scrubbing pads mentioned heretofore and many novel features that result in a new pumice scrubbing pad which is not anticipated, rendered obvious, suggested, or even implied by any of the prior art scrubbing pads, either alone or in any combination thereof.

It is another object of the present invention to provide a new pumice scrubbing pad which may be easily and efficiently manufactured and marketed.

It is a further object of the present invention to provide a new pumice scrubbing pad which is of a durable and reliable construction.

An even further object of the present invention is to provide a new pumice scrubbing pad which is susceptible of a low cost of manufacture with regard to both materials and labor, and which accordingly is then susceptible of low prices of sale to the consuming public, thereby making such pumice scrubbing pad economically available to the buying public.

Still yet another object of the present invention is to provide a new pumice scrubbing pad which provides in the apparatuses and methods of the prior art some of the advantages thereof, while simultaneously overcoming some of the disadvantages normally associated therewith.

Still another object of the present invention is to provide a new pumice scrubbing pad for removing rough and dead skin from feet.

Yet another object of the present invention is to provide a new pumice scrubbing pad which includes a plurality of filaments which are aggregated to form a pad member having spaces therein. Provided on the outer surface of the filaments is a scrubbing coating. The scrubbing coating includes a plurality scrubbing particles, a soap, a skin moisturizing agent, a fragrance, and a binder which couples the scrubbing coating to the outer surfaces of the filaments.

Still yet another object of the present invention is to provide a new pumice scrubbing pad that includes a soap, preferably an anti-fungal soap, to help keep a user's feet clean.

Even still another object of the present invention is to provide a new pumice scrubbing pad that includes an aloe base for moisturizing and helping keep a user's feet soft.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be made to the accompanying drawings and descriptive matter in which there are illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
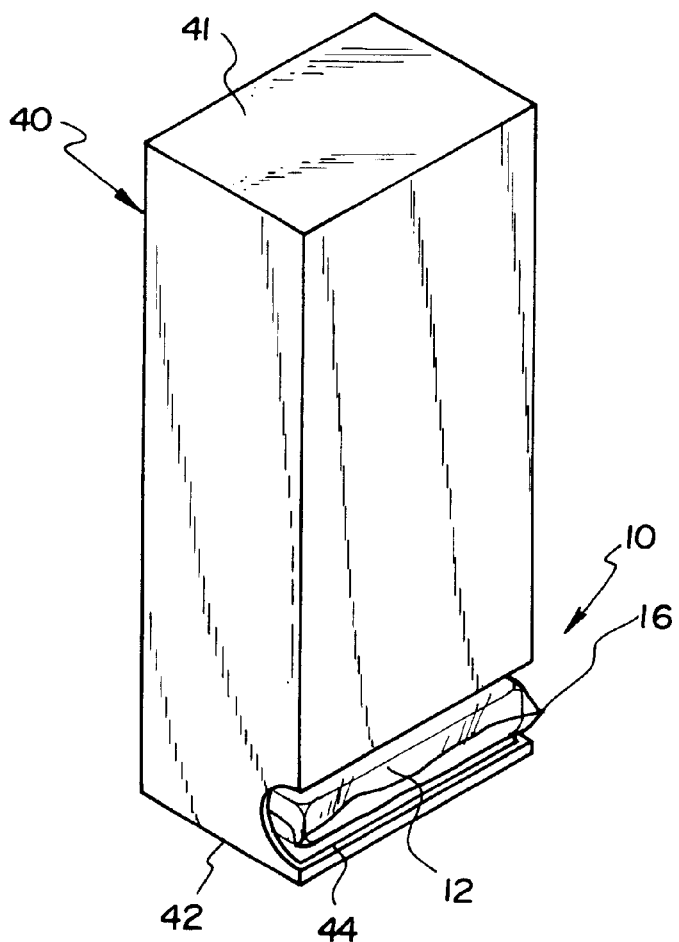
FIG. 1 is a schematic perspective view of a new pumice scrubbing pad in combination with a dispenser box according to the present invention.
Figure 2:
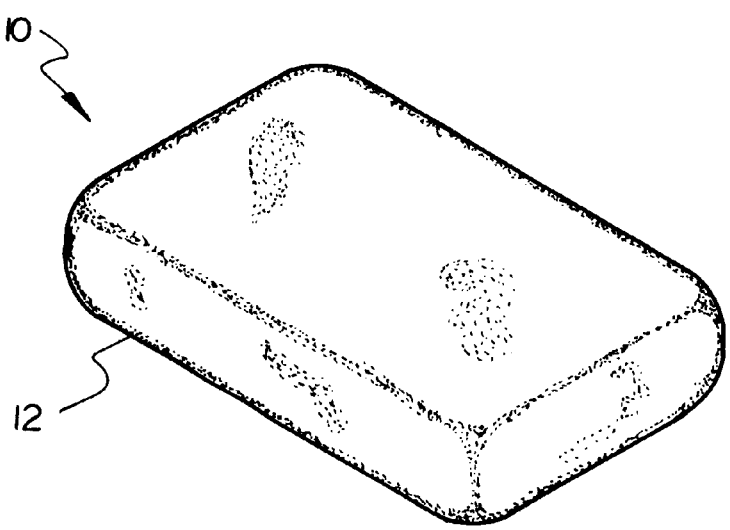
FIG. 2 is a schematic perspective view of a rectangle-shaped pumice scrubbing.

With reference now to the drawings, and in particular to FIGS. 1 through 5 thereof, a new pumice scrubbing pad embodying the principles and concepts of the present invention and generally designated by the reference numeral 10 will be described.

As best illustrated in FIGS. 1 through 5, the pumice scrubbing pad 10 generally comprises a plurality of filaments 20 which are aggregated to form a pad member 12 having spaces 14 therein. Provided on the outer surface of the filaments 20 is a scrubbing coating 30. The scrubbing coating 30 includes a plurality scrubbing particles, a soap, a skin moisturizing agent, a fragrance, and a binder which couples the scrubbing coating to the outer surfaces of the filaments 20.

Figure 3:
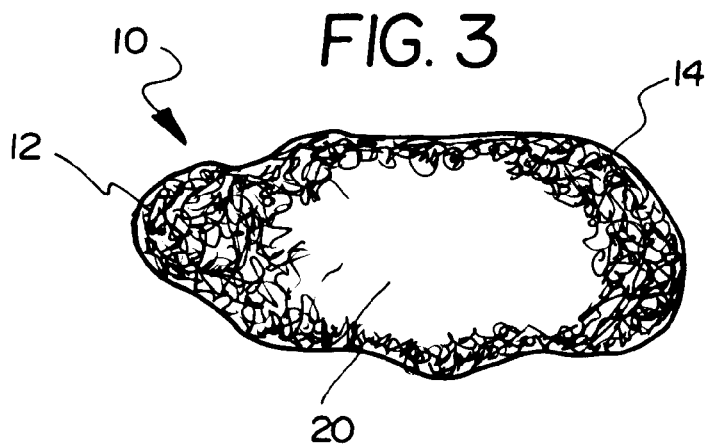
FIG. 3 is a schematic view of the present invention.

With reference to FIG. 3, the pad member 12 is formed from a plurality of aggregated filaments 20. Preferably, the filaments 20 are constructed from a fabric fiber such as cotton or a synthetic fiber such as nylon. The pad member 12 has a plurality of spaces 14, or interstices, therein for holding water and soap suds therein to aiding in the cleaning of a foot with the pumice scrubbing pad 10. Optionally, the pad member may being disposed within a protective wrapping 16 to help keep the pad 10 clean until use.

Figure 5:
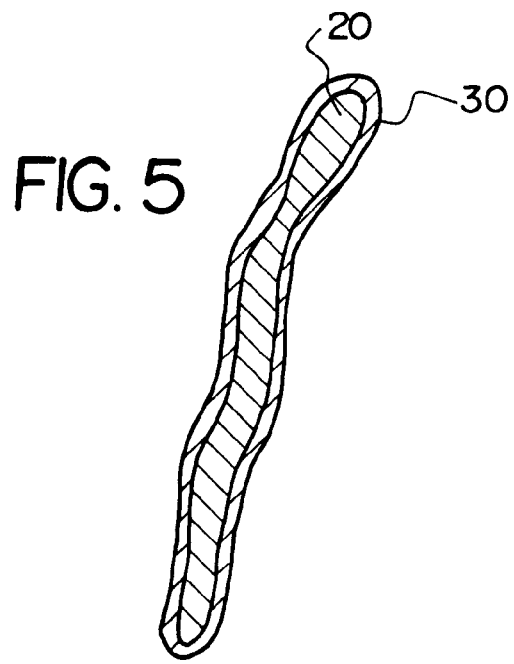
FIG. 5 is a schematic view of the present invention.
Figure 4:
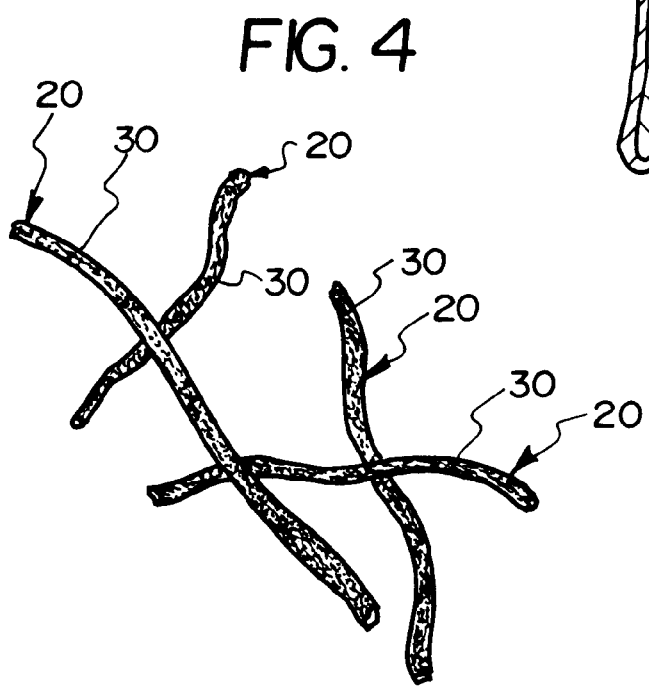
FIG. 4 is a schematic view of the present invention.

As illustrated on FIGS. 4 and 5, the scrubbing coating 30 is provided on the outer surfaces of each of the filaments 20. The scrubbing coating including a plurality scrubbing particles, a soap material, a skin moisturizing agent, a fragrance, and a binder. The binder couples the ingredients of the scrubbing coating (that is: the scrubbing particles, the skin moisturizing agent, and the fragrance) together and to the outer surfaces of the filaments 20.

The scrubbing particles are designed for scrubbing of dead skin from the surface of a foot. Preferably, the scrubbing particle comprise pumice particles (which can be made from pumice stone) appropriately sized to bind to the filaments 20. Optionally, pumice dust may be used for the scrubbing particles. The soap is designed for cleaning and disinfecting the skin. Preferably, the soap comprises a dried anti-fungal soap to help prevent fungal growth on the foot being scrubbed by the pad 10. The skin moisturizing agent is designed for moisturizing the feet. Preferably, the skin moisturizing agent comprises dried aloe moisturizing product. The fragrance is designed for aromatherapy, and may be any appropriate fragrance. Illustratively, appropriate fragrances includes peppermint, chamomile, lemon, and eucalyptus.

With reference to FIG. 1, the scrubbing pad 10 may be used in combination with a rectangular dispensing box 40 top and bottom ends 41,42. The box 40 is sized to fit a plurality of scrubbing pads 10 within the interior of the box 40. The box 40 has a slot 44 positioned towards it bottom end 42 for permitting removal (and insertion) of scrubbing pads 10 from (and into) the interior of the box 40.

In use, the pad 10 is wetted with water and then used to scrub the feet to clean and remove dead skin therefrom. The wetting of the pad helps release the soap within the pad and the spaces 14 in the pad member 12 help to form soap suds to develop a soap lather for cleaning the feet.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A scrubbing pad, comprising;
    a plurality of filaments, each of said filaments having an outer surface, said filaments being aggregated to form a pad member, said pad member having a plurality of spaces therein; and
    a scrubbing coating being provided on said outer surfaces of said filaments, said scrubbing coating including a plurality of scrubbing particles, a soap, a skin moisturizing agent, and a binder, said binder coupling said scrubbing coating to said outer surfaces of said filaments.

2. The scrubbing pad of claim 1, wherein said scrubbing particles comprise pumice particles.

3. The scrubbing pad of claim 1, wherein said soap comprises an anti-fungal soap.

4. The scrubbing pad of claim 1, wherein said skin moisturizing agent comprises aloe.

5. The scrubbing pad of claim 1, wherein said scrubbing coating further includes a fragrance.

6. The scrubbing pad of claim 5, wherein said fragrance is selected from the group comprising: peppermint, chamomile, lemon, and eucalyptus.

7. The scrubbing pad of claim 1, in combination with a dispensing box, said box being generally rectangular, said box having an interior, and top and bottom ends, a plurality of said scrubbing pads being disposable within said interior of said box, and said box having a slot being positioned towards said bottom end of said box.

8. A scrubbing pad, comprising;

a plurality of filaments, each of said filaments having an outer surface, said filaments being aggregated to form a pad member, said pad member having a plurality of spaces therein;

a scrubbing coating being provided on said outer surfaces of said filaments, said scrubbing coating including a plurality of scrubbing particles, a soap, a skin moisturizing agent, a fragrance, and a binder, said binder coupling said scrubbing coating to said outer surfaces of said filaments;

wherein said soap comprises an anti-fungal soap; and wherein said skin moisturizing agent comprises aloe.

9. A method for making a scrubbing pad, comprising the steps of:

providing a plurality of filaments, each of said filaments having an outer surface, applying a scrubbing coating on said outer surfaces of said filaments, said scrubbing coating including a plurality of scrubbing particles, a soap, a skin moisturizing agent, a fragrance, and a binder, said binder coupling said scrubbing coating to said outer surfaces of said filaments; and aggregating said filaments to form a pad member, said pad member having a plurality of spaces therein.

\* \* \* \* \*